United States Patent
Stucky et al.

(10) Patent No.: US 8,424,653 B2
(45) Date of Patent: Apr. 23, 2013

(54) ELECTRICAL SIGNAL APPLICATION STRATEGIES FOR MONITORING A CONDITION OF AN ELEVATOR LOAD BEARING MEMBER

(75) Inventors: Paul A. Stucky, Stockton, CA (US); Michael A. Kryzman, West Hartford, CT (US); William A. Veronesi, Hartford, CT (US)

(73) Assignee: Otis Elevator Company, Farmington, CT (US)

( * ) Notice: Subject to any disclaimer, the term of this patent is extended or adjusted under 35 U.S.C. 154(b) by 70 days.

(21) Appl. No.: 13/195,902

(22) Filed: Aug. 2, 2011

(65) Prior Publication Data

US 2011/0284331 A1  Nov. 24, 2011

Related U.S. Application Data

(63) Continuation of application No. 10/598,044, filed as application No. PCT/US2004/007900 on Mar. 16, 2004, now Pat. No. 8,011,479.

(51) Int. Cl.
*B66B 3/00* (2006.01)

(52) U.S. Cl.
USPC .......................... 187/393; 187/391; 187/392

(58) Field of Classification Search ........... 187/391–393
See application file for complete search history.

(56) References Cited

U.S. PATENT DOCUMENTS

| | | | |
|---|---|---|---|
| 3,958,455 A | 5/1976 | Russell | |
| 4,291,204 A | 9/1981 | Crick | |
| 4,491,782 A | 1/1985 | Bellis et al. | |
| 4,785,914 A | 11/1988 | Blain et al. | |
| 5,189,375 A | 2/1993 | Tuttle | |
| 5,331,286 A | 7/1994 | Rivola et al. | |
| 5,338,417 A | 8/1994 | Brucken et al. | |

(Continued)

FOREIGN PATENT DOCUMENTS

| | | |
|---|---|---|
| DE | 3934654 A1 | 5/1991 |
| EP | 0210509 A1 | 2/1987 |
| WO | 0058706 | 10/2000 |
| WO | WO0058706 A3 * | 10/2000 |

OTHER PUBLICATIONS

International Search Report for International application No. PCT/US04/07900 dated May 15, 2006.

(Continued)

*Primary Examiner* — Kawing Chan
(74) *Attorney, Agent, or Firm* — Carlson, Gaskey & Olds PC

(57) ABSTRACT

An elevator load bearing member (30) monitoring device includes a controller (42) that applies a selected electrical signal to tension members (32) of the load bearing member (30). In one example, connectors (40) are associated with ends of the load bearing member (30) to establish an electrical interface between the controller (42) and the tension members (32). The connectors (40) facilitate establishing electrical circuit loops along the tension members (32) such that only non-adjacent tension members are energized at a selected time. A variety of circuit configurations are disclosed. The applied electrical signal in one example has a potential that is negative compared to a ground potential of a hoistway in which the elevator belt is used. In another example, the electrical signal comprises a plurality of pulses and has a duty cycle that is on the order of about one percent.

17 Claims, 4 Drawing Sheets

U.S. PATENT DOCUMENTS

| | | | |
|---|---|---|---|
| 5,731,528 A | 3/1998 | Yamazaki et al. | |
| 5,890,564 A | 4/1999 | Olsen et al. | |
| 6,073,728 A | 6/2000 | Olsen et al. | |
| 6,601,448 B1 | 8/2003 | Bernard et al. | |
| 6,633,159 B1 * | 10/2003 | Robar et al. | 324/240 |
| 6,653,943 B2 | 11/2003 | Lamb et al. | |
| 7,023,680 B1 | 4/2006 | Johnson et al. | |
| 7,123,030 B2 * | 10/2006 | Robar et al. | 324/693 |
| 7,409,870 B2 | 8/2008 | Stucky et al. | |
| 7,410,033 B2 * | 8/2008 | Veronesi et al. | 187/391 |
| 7,506,728 B2 | 3/2009 | Hawkes et al. | |
| 2002/0194935 A1 * | 12/2002 | Clarke et al. | 73/862.391 |
| 2003/0011483 A1 * | 1/2003 | Lamb et al. | 340/664 |
| 2003/0121729 A1 | 7/2003 | Heinz et al. | |
| 2004/0026177 A1 | 2/2004 | Ayano et al. | |
| 2007/0181385 A1 * | 8/2007 | Veronesi et al. | 187/413 |
| 2011/0000746 A1 * | 1/2011 | Pelto-Huikko et al. | 187/254 |

OTHER PUBLICATIONS

Written Opinion of the International Searching Authority for International application No. PCT/US04/07900 dated May 15, 2006.

* cited by examiner

ELECTRICAL SIGNAL APPLICATION STRATEGIES FOR MONITORING A CONDITION OF AN ELEVATOR LOAD BEARING MEMBER

CROSS-REFERENCE TO RELATED APPLICATIONS

This application is a continuation of U.S. patent application Ser. No. 10/598,044, filed Aug. 16, 2006, now U.S. Pat. No. 8,011,479, which is the national stage application of PCT/US2004/007900 filed 16 Mar. 2004.

FIELD OF THE INVENTION

This invention generally relates to monitoring load bearing members in elevator systems. More particularly, this invention relates to a circuit arrangement for using electricity-based monitoring techniques.

DESCRIPTION OF THE RELATED ART

Elevator systems often include a car and counterweight that are suspended by a rope or belt arrangement. A drive machine moves the rope or belt to cause the desired movement of the car to different levels within a building, for example. Traditionally, steel ropes were used. More recently, other types of load bearing assemblies have been introduced. One example is a coated steel belt having a plurality of steel cords encased in a polyurethane jacket.

With the introduction of new belts, the need for new monitoring techniques has arisen to check the quality of the belt over time. The jackets over the tension members prevent visual inspection. Coated steel belts are believed to have extended service lives, however, it is advisable to monitor the condition of them to detect any degradation in the strength of the tension members within the belt (i.e., the steel cords). A variety of monitoring techniques are being developed.

One approach is to use electricity for determining the characteristics of the tension members and, therefore, the strength of the belt. One example technique relies upon the fact that the cross-sectional area of a steel cord tension member is directly related to the electrical resistance of that member. Accordingly, monitoring the resistance of the tension members provides an indication of the condition of the tension members.

In order to utilize a resistance based inspection technique, an efficient strategy is required for arranging electrical circuits so that the resistance of the tension members can be determined. This invention addresses that need by providing unique circuit arrangements and strategic electrical signal characteristics to enable effective monitoring of the tension members in a coated steel belt, for example.

SUMMARY OF THE INVENTION

In general terms, this invention is a circuit arrangement that enables efficient electricity-based monitoring of an elevator load bearing member.

One example method includes applying an electric signal that comprises a plurality of pulses and has a duty ratio that is less than about ten percent to at least one of the tension members. In one example, the duty cycle is less than about one percent. A low duty ratio minimizes the amount of electrical energy carried by the tension members, which tends to reduce the possibility for any corrosion resulting from using the tension members as conductors of electricity.

Where a load bearing member has a plurality of spaced, electrically conductive tension members, an example method includes strategically applying electric signals only to tension members that are not adjacent to each other to avoid establishing an electric field between the spaced apart tension members. This technique avoids any corrosion or degradation of the tension members that may otherwise be caused by the introduction of electricity along the tension members.

In one example, at least two non-adjacent tension members are electrically coupled so that the electric signal is applied to the coupled tension members, which form a loop or circuit along which the electric signal is propagated.

According to one example, the electric signal applied to the tension members is chosen so that the tension members are effectively cathodes relative to a hoistway where the load bearing member is used. This is accomplished in one example by controlling a potential of the electrical signal such that the potential is negative compared to a ground potential of the hoistway.

In another example, the electric signal is applied only to non-adjacent tension members at a given time.

The various features and advantages of this invention will become apparent to those skilled in the art from the following detailed description of the currently preferred embodiment. The drawings that accompany the detailed description can be briefly described as follows.

DETAILED DESCRIPTION OF THE PREFERRED EMBODIMENTS

Figure 1:
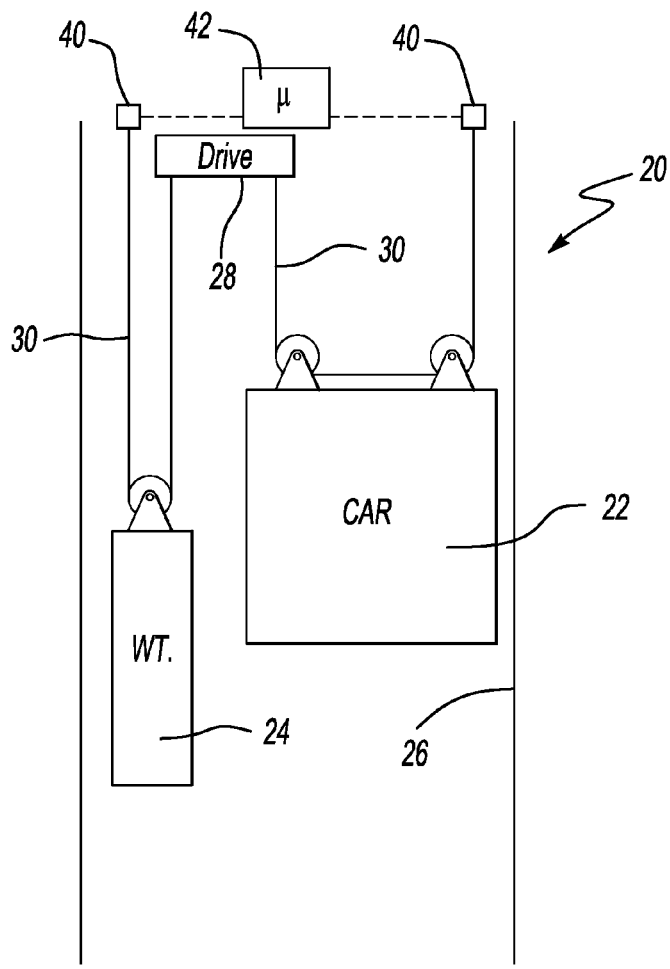
FIG. 1 schematically illustrates selected portions of an elevator system including an elevator load bearing member monitoring assembly designed according to an embodiment of this invention.

FIG. 1 schematically shows an elevator system 20 where a car 22 and counterweight 24 move within a hoistway 26. A drive machine 28 causes movement of a load bearing member 30, which results in the desired movement of the car 22 and corresponding movement of the counterweight 24. The movement of the elevator system is known.

Figure 2:
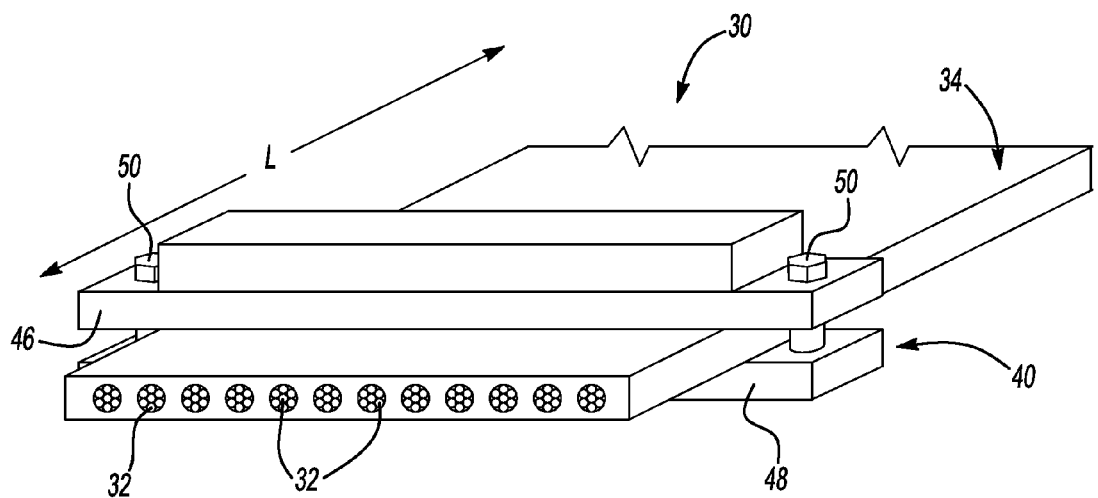
FIG. 2 is a perspective illustration of a portion of an elevator belt schematically illustrating an electrical connector useful with an embodiment of this invention.

As shown in FIG. 2, an example load bearing member 30 is a coated steel belt having a plurality of steel cord tension members 32 encased in a polyurethane jacket 34. As can be appreciated form the drawing, the tension members 32 comprise a plurality of steel strands wound into a cord in a known manner. The jacket material 34 generally surrounds each of the tension members and fills spaces between them. The tension members 32 extend longitudinally (as shown by L in FIG. 2) in parallel along the length of the belt 30. This invention is not limited to a specific kind of load bearing member.

FIG. 2 also shows a connector 40 for establishing an electrical connection with the tension members 32. Although not specifically illustrated, in one example the connector 40 includes connector members that pierce through the jacket material 34 to establish an electrical connection with at least selected ones of the tension members 32. The connectors 40 in the example of FIG. 1 are attached to each end of the belt 30 and provide an electrical interface for coupling the tension members 32 with a controller 42 that is suitably programmed to conduct a selected electricity-based monitoring technique. The example connector 40 includes a first portion 46 and a second portion 48 received on opposite sides of the belt 30. Securing members 50 allow the connectors 40 to be secured in a desired position near the ends of the example belt 30.

The controller 42 preferably monitors the condition of the tension members 32 and, therefore, the condition of the belt 30 by monitoring a selected electrical characteristic of the tension members. In one example, the resistance of each tension member is monitored to make determinations regarding the cross-sectional area of the tension members, which provides an indication of localized strain or degradation of the tension members over time. This description includes a variety of circuit arrangements for enabling the controller 42 to make the necessary determinations.

The example controller 42 includes an ohm-meter portion 44 that makes a determination regarding the electrical resistance of the tension members 32, respectively.

Figure 3:
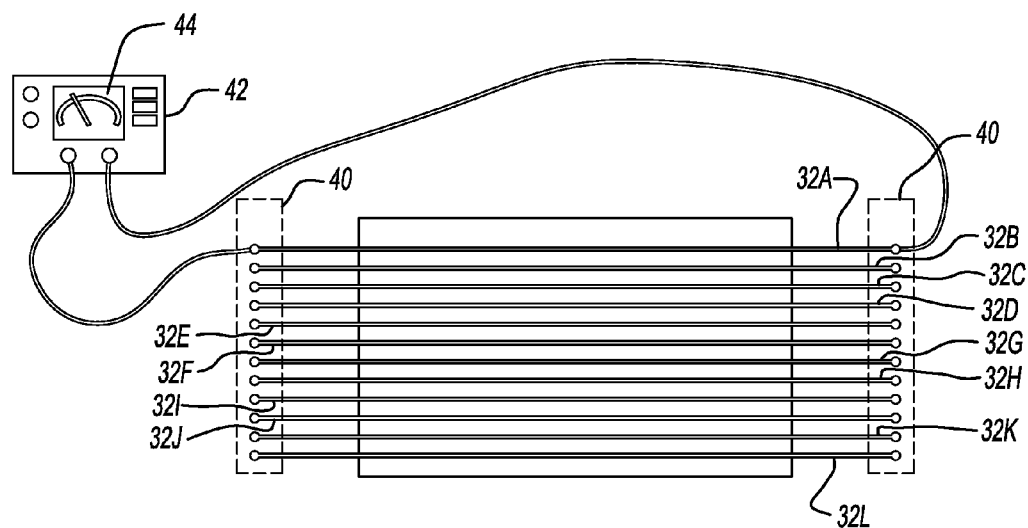
FIG. 3 schematically illustrates an example circuit configuration designed according to an embodiment of this invention.

FIG. 3 schematically illustrates one example circuit geometry designed according to an embodiment of this invention. In this example, each tension member 32A-32L is individually coupled with the controller 42. Each tension member accordingly establishes its own circuit as schematically shown in FIG. 3 (although the connections between the controller 42 and the tension member 32A are the only connections specifically illustrated). A similar connection is made with each of the individual tension members. One advantage to such an arrangement is that it allows for individually monitoring any one of the tension members. Alternatively, such an arrangement allows for monitoring every tension member simultaneously. If all tension members are powered appropriately, there is no inter-cord corrosion risk as there would be no potential difference between the tension members.

One possible source of corrosion risk may occur when a sufficient electric field is established between the cords such that ions may migrate between tension members. Minimizing such migrating ions minimizes corrosion risk.

Figure 4:
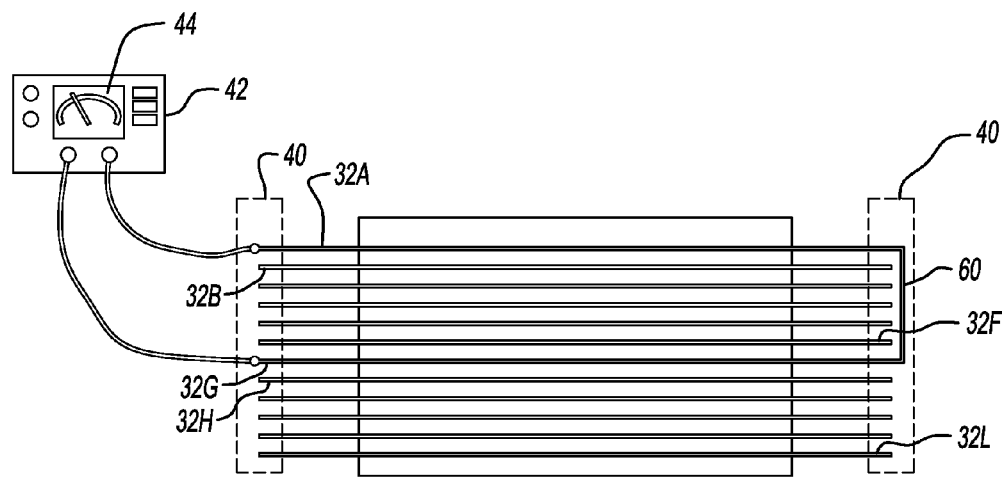
FIG. 4 schematically illustrates another circuit configuration.

Another example arrangement is shown in FIG. 4 where the tension members 32A and 32G establish a single circuit loop that is monitored as the controller 42 applies an electrical signal to that circuit. In this example, one of the connectors 40 establishes the interface with the controller 42. The other connector 40 includes an electric coupling 60 that couples the tension members 32A and 32G together to establish the circuit loop. In this example, the tension members are grouped in six sets of two so that the first and seventh (i.e., 32A, 32G) tension members form one circuit while the second and eighth form another circuit. Similarly, the sixth and twelfth tension members form a circuit. Using such a strategy maintains maximum distance between two tension members that are energized simultaneously for carrying an electric signal applied by the controller 42. Maintaining a maximum distance between the conducting tension members minimizes the corrosion risks associated with migrating ions that may migrate across the belt 30 because of the electric field established between tension members. By utilizing non-adjacent tension members to establish a circuit loop, the inventive approach minimizes the risk of corrosion otherwise associated with the application of electricity to the tension members.

It should be noted that FIG. 4 shows only one electrical coupling 60 although six of them are used to establish the six separately circuit loops along the belt 30. One advantage to an arrangement as shown in FIG. 4 is that only one of the connectors 40 is required for making an actual connection with the controller 42, which minimizes the complexity or expense of the electrical coupling (i.e., wiring) between the connectors 40 and the controller 42. The electrical couplings 60 within the connector 40 at one end of the belt 30 can effectively be internal to the connector so that no outside wiring is required near that end of the belt.

Figure 5:
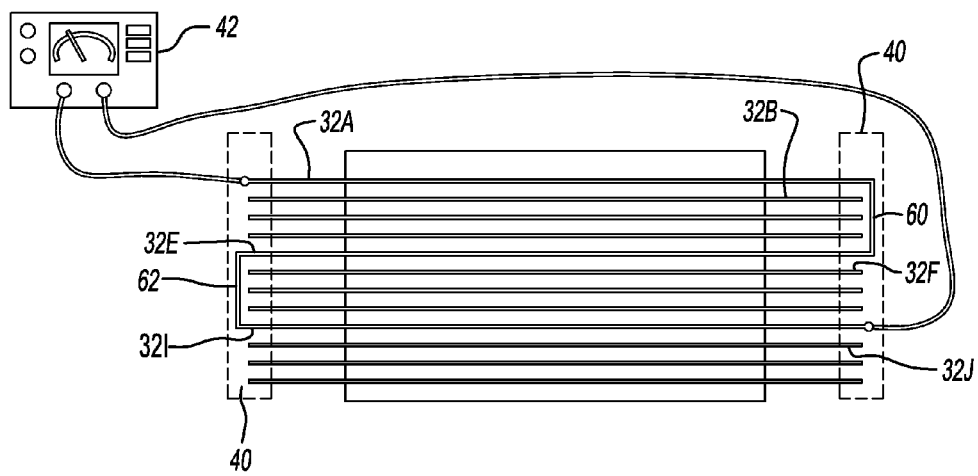
FIG. 5 illustrates another circuit configuration.

FIG. 5 illustrates another example circuit arrangement. In this example, four groups of three tension members are electrically coupled using electrical couplings 60 and 62 to establish circuit loops. In some instances, the length of the belt 30 may be too short for an individual tension member (or even two tension members) to establish a circuit long enough to achieve a signal-to-noise ratio that enables accurate enough monitoring. An arrangement as shown in FIG. 5 facilitates establishing a better signal-to-noise ratio for relatively shorter belts by increasing the number of tension members within a single circuit loop. In this example, the tension members 32A, 32E and 32I establish a first circuit loop. The tension members 32B, 32F and 32J establish another loop. Similarly, two additional loops are established with the preference to maintain a maximum feasible distance between tension members that will be energized at any given time. By energizing only non-adjacent tension members, the inventive approach minimizes the risk of corrosion of the tension members.

Figure 6:
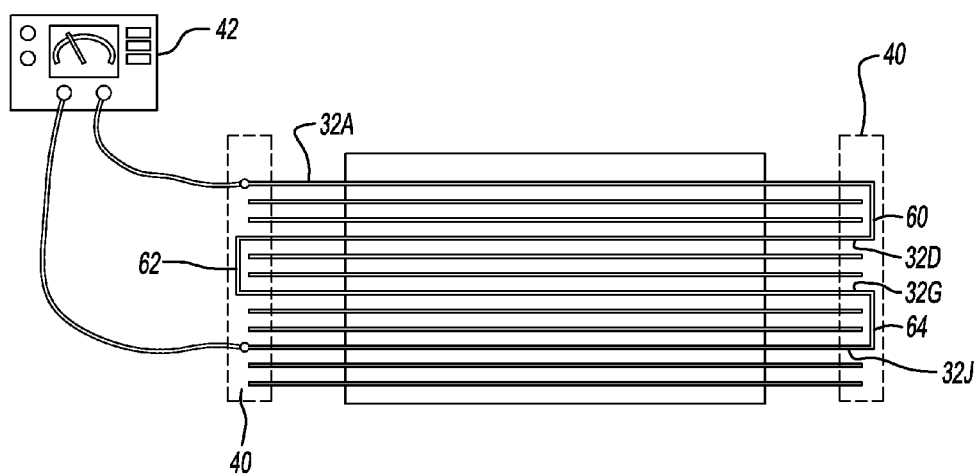
FIG. 6 illustrates another example circuit configuration.

FIG. 6 illustrates another example that has the advantage like FIG. 4 where the connections with the controller 42 are established by a single one of the connectors 40. In this example, four tension members 32A, 32D, 32G and 32J establish a single circuit loop. Three electrical couplings, 60, 62 and 64, are required to establish the loop. One of the connectors 40 includes the couplings 60 and 64 and does not require any external wiring, which may be advantageous in many circumstances. Although not specifically illustrated, an arrangement as shown in FIG. 6 used with a belt having twelve tension members preferably includes three sets of four tension members coupled into a single circuit loop.

Figure 7:
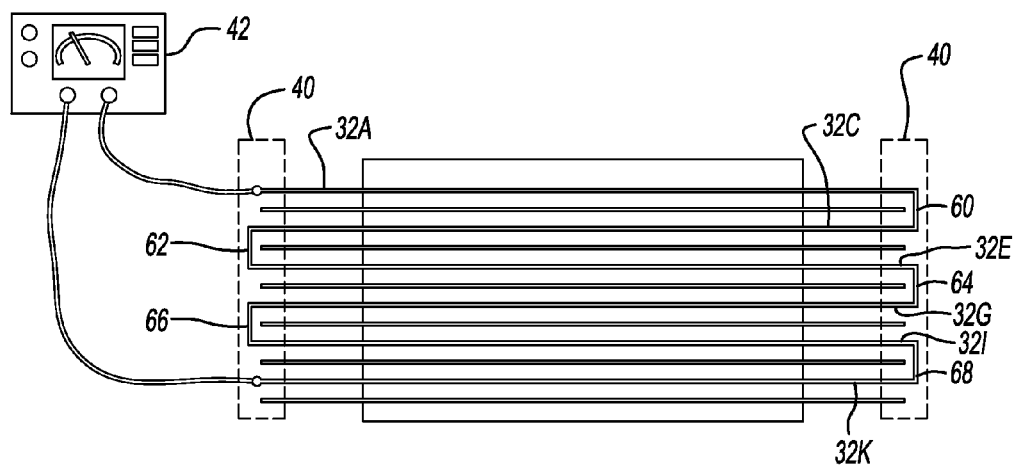
FIG. 7 illustrates another example circuit configuration.

FIG. 7 illustrates still another example where two circuit loops are established by electrically coupling six of the tension members together into a single circuit loop. In FIG. 7, the tension members 32A, 32C, 32E, 32G, 32I and 32K are coupled together into a single circuit loop. Electrical couplings 60, 62, 64, 66 and 68 establish the circuit loop. The other tension members are grouped into a second circuit. Such an arrangement minimizes the number of circuits that need to be monitored using the controller 42. The distance between tension members energized at the same time is reduced compared to the example of FIG. 4, for example, however this may be advantageous, depending on the needs of a given situation. Those skilled in the art who have the benefit of this description will be able to select an appropriate arrangement to best meet the needs of their particular situation.

In each of the described examples, the belt 30 has twelve tension members extending along the length of the belt. Of course, other circuit arrangements for different numbers of tension members may be more beneficial. Those skilled in the art who have the benefit of this description will realize what circuit arrangement works best for their particular situation.

Another feature of some examples is to strategically control the electrical signal applied to the tension members 32 to further reduce the risk of corrosion. Increasing the lateral distance between the tension members that have an electrical potential difference between them is one technique for reducing the possibility for establishing a conducting electrolytic pathway between energized cords. Another feature of some examples is to limit the maximum operating potential applied to the tension members 32. In one example, the maximum voltage is 2 volts. An effective monitoring signal may have a potential between 0 and 2 volts, for example.

In another example, the electrical signal comprises a plurality of pulses and has a very low duty cycle so that the "on" time of the signal is very low. In one example, the duty cycle is less than or equal to about one percent, which minimizes the time during which the electrical potential is applied to the tension members 32. Minimizing the on time of the electrical signal further minimizes the possible corrosion risk.

In another example, the electrical signal is selected to have a polarity that establishes the tension members 32 as cathodes relative to the environment in which the belt 32 is used. For example, the electrical polarity of the signal is negative compared to the effective ground of the hoistway 26. Applying an electrical signal of this characteristic reduces a corrosion risk in the event that a stray current pathway were established between the tension members and the hoistway or building ground.

A variety of techniques for minimizing the corrosion risk that otherwise may be present when applying electricity to the tension members in an elevator load bearing member have been described. A combination of two or more of the above-described techniques further reduces the corrosion risk and enables efficient electricity-based monitoring of an elevator belt.

The preceding description is exemplary rather than limiting in nature. Variations and modifications to the disclosed examples may become apparent to those skilled in the art that do not necessarily depart from the essence of this invention. The scope of legal protection given to this invention can only be determined by studying the following claims.

We claim:

1. A method of monitoring a condition of an elevator belt having a plurality of spaced, electrically conductive tension members in a jacket, the method comprising the steps of:
    (a) electrically coupling at least some of the tension members to each other into at least two circuits;
    (b) applying a selected electric signal to the circuits; and
    (c) determining the condition of the belt based upon the applied signals.

2. The method of claim 1, wherein the tension members comprise cords.

3. The method of claim 1, wherein the applying step occurs on one circuit at a time.

4. The method of claim 1, wherein the determining step includes determining a resistance of the circuits.

5. A method of monitoring a condition of an elevator belt having a plurality of spaced, electrically conductive tension members in a jacket, the method comprising the steps of:
    (a) electrically coupling at least some of the tension members into at least two circuits by coupling non-adjacent tension members into one of the at least two circuits;
    (b) applying a selected electric signal to the circuits; and
    (c) determining the condition of the belt based upon the applied signals.

6. A device for monitoring a condition of an elevator belt having a plurality of spaced, electrically conductive tension members in a jacket, the device comprising:
    a plurality of electric couplings that arrange at least some of the tension members into at least two circuits, each of the circuits including at least two of the tension members electrically coupled together; and
    a controller that applies a selected electric signal to the circuits and determines a condition of the belt based on the applied signal.

7. The device of claim 6, wherein the couplings comprise connectors.

8. The device of claim 6, wherein the tension members comprise cords.

9. The device of claim 6, wherein the controller applies the signal to one circuit at a time.

10. The device of claim 6, wherein the controller determines a resistance of the circuits.

11. A device for monitoring a condition of an elevator belt having a plurality of spaced, electrically conductive tension members in a jacket, the device comprising:
    a plurality of electric couplings that arrange at least some of the tension members into at least two circuits, wherein the couplings couple non-adjacent tension members into one of the at least two circuits; and
    a controller that applies a selected electric signal to the circuits and determines a condition of the belt based on the applied signal.

12. An assembly, comprising:
    (a) an elevator belt having:
        (i) a jacket; and
        (ii) a plurality of spaced, electrically conductive tension members in the jacket; and
    (b) a monitoring device having:
        (i) a plurality of electric couplings that arrange at least some of the tension members into at least two circuits, each of the circuits including at least two of the tension members electrically coupled together; and
        (ii) a controller that applies a selected electric signal to the circuits and determines a condition of the belt based on the applied signal.

13. The device of claim 12, wherein the couplings comprise connectors.

14. The device of claim 12, wherein the tension members comprise cords.

15. The device of claim 12, wherein the controller applies the signal to one circuit at a time.

16. The device of claim 12, wherein the controller determines a resistance of the circuits.

17. An assembly, comprising:
    (a) an elevator belt having:
        (i) a jacket; and
        (iii) a plurality of spaced, electrically conductive tension members in the jacket; and
    (b) a monitoring device having:
        (i) a plurality of electric couplings that arrange at least some of the tension members into at least two circuits, wherein the couplings couple non-adjacent tension members into one of the at least two circuits; and
        (ii) a controller that applies a selected electric signal to the circuits and determines a condition of the belt based on the applied signal.

* * * * *